(12) United States Patent
Brammer

(10) Patent No.: US 10,981,851 B2
(45) Date of Patent: Apr. 20, 2021

(54) HYDROFORMYLATION PROCESS

(71) Applicant: Dow Technology Investments LLC, Midland, MI (US)

(72) Inventor: Michael A. Brammer, Freeport, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 16/631,555

(22) PCT Filed: Oct. 3, 2018

(86) PCT No.: PCT/US2018/054062
§ 371 (c)(1),
(2) Date: Jan. 16, 2020

(87) PCT Pub. No.: WO2019/083700
PCT Pub. Date: May 2, 2019

(65) Prior Publication Data
US 2020/0247741 A1 Aug. 6, 2020

Related U.S. Application Data

(60) Provisional application No. 62/576,867, filed on Oct. 25, 2017.

(51) Int. Cl.
*C07C 45/50* (2006.01)
*B01J 31/24* (2006.01)

(52) U.S. Cl.
CPC .......... *C07C 45/50* (2013.01); *B01J 31/2404* (2013.01); *B01J 2531/822* (2013.01)

(58) Field of Classification Search
CPC ................ C07C 45/50; B01J 2531/822; B01J 2531/845
See application file for complete search history.

(56) References Cited

U.S. PATENT DOCUMENTS

| | | |
|---|---|---|
| 4,148,830 A | 4/1979 | Pruett et al. |
| 4,247,486 A | 1/1981 | Brewester et al. |
| 4,567,306 A | 1/1986 | Dennis et al. |
| 4,774,361 A | 9/1988 | Maher et al. |
| 5,183,943 A | 2/1993 | Bryant et al. |
| 5,731,472 A | 3/1998 | Leung et al. |
| 5,741,942 A | 4/1998 | Bryant et al. |
| 5,741,944 A | 4/1998 | Bryant et al. |
| 5,876,640 A | 3/1999 | Miyahara et al. |
| 7,232,931 B2 | 6/2007 | Toetsch et al. |
| 9,353,032 B2 | 5/2016 | Eisenacher et al. |
| 2015/0376101 A1 | 12/2015 | Eisenschmid |

FOREIGN PATENT DOCUMENTS

| | | |
|---|---|---|
| WO | 2014/149915 A1 | 9/2014 |
| WO | 2015/153070 A1 | 10/2015 |

OTHER PUBLICATIONS

Van Leeuwen, Peit. EDS. "Rhodium Catalyzed Hydroformylation," van Leeuwen, Claver, Kluwer Academic Pub. Chapters 3, 8 and 9 2000.
Tolman, Chadwick A., Steric Effects of Phosphorus Ligands in Organometallic Chemistry and Homogeneous Catalysis, Chemical Reviews, 77(3), 313-348, 1977.
PCT/US2018/054062, International Search Report and Written Opinion dated Nov. 28, 2018.
Miller, Journal of American Chemical Society, 1962, vol. 84, pp. 3775-3777.

*Primary Examiner* — Sikarl A Witherspoon

(57) ABSTRACT

Some embodiments of the present invention relate to processes for reducing heavies formation in a solution comprising one or more aldehydes, such as a reaction fluid in a hydroformylation process. In some embodiments, the process comprises providing 0.1 to 5 wt. percent of an organic nitrogen compound based on the total weight of the aldehyde solution, the organic nitrogen compound comprising: wherein each of R1-R5 are independently hydrogen, an alkyl, or an aryl radical.

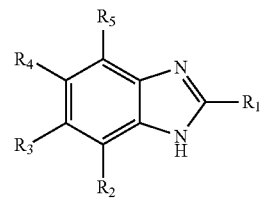

11 Claims, No Drawings

HYDROFORMYLATION PROCESS

FIELD

The present invention relates to processes for reducing heavies formation in an aldehyde solution including, for example, the reduction of heavies in an aldehyde solution in a hydroformylation process.

BACKGROUND

It is well known that continuous hydroformylation processes will slowly form relatively high-boiling aldehyde-derived byproducts over time (see, e.g., U.S. Pat. Nos. 4,148,830 and 4,247,486). Because these "heavies" often serve as the reaction solvent, they are initially allowed to accumulate in liquid recycle processes, but adjustments in product separation conditions (e.g. temperature, pressure, strip gas flow rate, etc.) must be made to prevent their concentration from increasing beyond practical limits. Establishing a ratio of reactor effluent (feed) introduced to the separation zone relative to the non-volatiles returned to the reaction zone (tails) while still maintaining the desired aldehyde production rate will ultimately determine the maximum concentration of heavies that the system may sustain. Once the heavies concentration limit is reached, they must be removed at a rate comparable to their formation rate to maintain the desired balance. A currently preferred method of heavies removal is volatilization; however, if the byproducts in question are too high-boiling to distill overhead (e.g., derived from higher olefins), it may be necessary to remove them from the system as a liquid purge stream (e.g., removal of separation zone liquid effluent) to extend catalyst life. Costs are associated with the liquid purge, including precious metal recovery of the contained rhodium, loss of ligand, and potential loss of product aldehyde (see, e.g., U.S. Pat. No. 7,232,931).

Although the presence of impurities (e.g. metals, acids, bases, etc.) can catalyze side reactions, under normal circumstances, the primary driver for heavies formation is elevated temperatures. Even when heavies may be removed via volatilization at their formation rate, they still represent a source of product inefficiency. Thus, losses due to the presence of heavies is a consideration when establishing acceptable reactor temperatures, even in processes employing lower carbon number olefins.

Thus, alternative means for the reduction of heavies in a hydroformylation process, particularly in the hydroformylation of higher olefins, is desirable.

SUMMARY

It has surprisingly been discovered that the addition of a certain class of organic nitrogen compound will slow the rate of aldehyde-derived heavy byproducts in an aldehyde solution such as a reaction fluid in a hydroformylation process. Ordinarily the addition of nitrogen-containing species would be expected to cause increased heavies formation by base-catalyzed aldol condensation but this class not only does not increase the rate of heavies formation but surprisingly lowers the rate of heavies formation even in the absence of hydroformylation catalyst. In some embodiments, processes of the present invention have a further advantage of reducing the loss of rhodium in catalyst solutions utilizing organomonophosphites as ligands.

In one aspect, the present invention relates to a process to reduce heavies formation in a solution comprising one or more aldehydes, the process comprising providing 0.1 to 5 wt. percent of an organic nitrogen compound based on the total weight of the aldehyde solution, the organic nitrogen compound comprising:

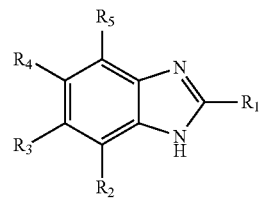

wherein each of $R_1$-$R_5$ are independently hydrogen, an alkyl, or an aryl radical.

In another aspect, the present invention relates to a process to reduce heavies formation in a hydroformylation process to produce at least one aldehyde, the process comprising contacting in a reaction zone reactants comprising an olefin, hydrogen and carbon monoxide in the presence of a catalyst comprising an organomonophosphite ligand and at least one of rhodium and cobalt, and 0.1 to 5 weight percent of an organic nitrogen compound based on the total weight of fluid in the reaction zone, the organic nitrogen compound comprising:

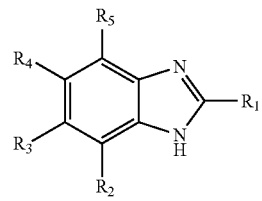

wherein each of $R_1$-$R_5$ are independently hydrogen, an alkyl, or an aryl radical, wherein a plurality of heavies are formed during the hydroformylation process, wherein the rate of heavies formation is at least 10 percent less than the rate of heavies formation of when the process is carried out in the absence of the organic nitrogen compound, and wherein the hydroformylation process is a continuous process and the rate of heavies formation is measured using gas chromatography over a period of at least seven days.

These and other embodiments are discussed in more detail in the Detailed Description below.

DETAILED DESCRIPTION

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the terms "ppm" and "ppmw" are used interchangeably and mean parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the terms "hydroformylation" or "hydroformylation process" are contemplated to include, but are not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds, which may be dissolved and/or suspended, formed in the reaction. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an acid removal system such as an extractor or other immiscible fluid contacting system, (g) a treated or untreated fluid returned to a reaction zone or separation zone, (h) a fluid in an external cooler, and (i) ligand decomposition products and components derived from them, such as oxides, sulfides, salts, oligomers, and the like.

"Organomonophosphite ligands" are compounds containing a single phosphorous atom bound to three oxygen atoms; the three oxygen atoms are each additionally bound to carbon moieties. Illustrative examples include, but are not limited to monoorganophosphite, diorganophosphite, triorganophosphite compounds, examples of which include: tris (2,4-di-t-butylphenyl)phosphite, 4,8-di-tert-butyl-6-(2-(tert-butyl)-4-methoxyphenyl)-2,10-dimethoxydibenzo[d][1,3,2] dioxaphosphepine, and the like.

For the purposes of the invention, a "bulky organomonophosphite" or a "sterically hindered organomonophosphite" is an organomonophosphite with a Tolman steric parameter of 135 to 190°. The Tolman steric parameter is defined as the apex angle of a cylindrical cone, centered at a position of 2.28 angstroms apart from the center of the phosphorous atom, which just touches the Van der Waals radii of the atoms most externally present in the groups bonded to the phosphorous atom, as set forth in Tolman, CHEM. REV., 177, 313 (1977). "Hydrolyzable organophosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, phosphonites, phosphinites, phosphoramidites, phosphino-phosphoramidites, fluorophosphites, and the like.

The term "free ligand" means ligand that is not complexed with (or bound to) the metal, e.g., metal atom, of the complex catalyst.

For the purposes of this invention, the terms "heavy byproducts" and "heavies" are used interchangeably and refer to liquid byproducts that have a normal boiling point that is at least 25° C. above the normal boiling point of the desired product of the hydroformylation process. Such materials are known to form in hydroformylation processes under normal operation through one or more side reactions, including for example, by aldol condensation.

For the purpose of this invention, the term "dimer" when referring to heavy byproducts from a hydroformylation reaction refers to heavy byproducts derived from two molecules of aldehyde. Likewise the term "trimer" when referring to heavy byproducts from a hydroformylation reaction refers to heavy byproducts derived from three molecules of aldehyde.

For the purposes of this invention, the terms "separation zone" and "vaporizer" are used interchangeably and refer to a separation device wherein the product aldehyde is typically volatilized overhead, condensed and collected, while the non-volatile concentrated effluent (tails, or vaporizer tails) containing the homogeneous catalyst is returned to one or more of the reactors. The vaporizer temperature is typically higher than the reactor temperature, and may optionally be operated at reduced pressure. In one embodiment, the vaporizer features flowing gas of varying composition that aids in product removal and optionally helps stabilize the catalyst ("strip gas vaporizer"). Other separation zone processes such as liquid/liquid extraction or membrane filtration may also be employed.

For the purposes of this invention, the terms "feed to tails" and "feed to tails ratio" are used interchangeably and refer to the mass of reaction fluid entering the separation zone relative to the mass of vaporizer tails leaving the separation zone and returning to the hydroformylation reactors. "Feed to tails" is an indicator of the rate at which volatiles, such as aldehyde product, are removed from the reaction fluid. For example, a "feed to tails ratio" of 2, means that the weight of reaction fluid entering the separation zone is two times greater than the weight of the concentrated effluent returned to the hydroformylation reactors.

Some embodiments of the present invention relate to processes for reducing heavies formation in a solution comprising one more aldehydes. In some embodiments a process to reduce heavies formation in a solution comprising one or more aldehydes comprises providing 0.1 to 5 wt. percent of an organic nitrogen compound based on the total weight of the aldehyde solution, the organic nitrogen compound comprising:

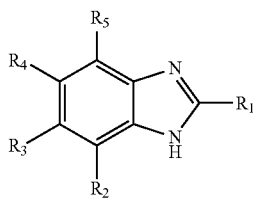

wherein each of $R_1$-$R_5$ are independently hydrogen, an alkyl, or an aryl radical. In some embodiments, the organic nitrogen compound comprises benzimidazole. In some embodiments, the aldehydes in the solution are $C_3$ or higher.

In some embodiments, the aldehyde solution is a reaction fluid in a hydroformylation process that comprises an olefin, hydrogen, carbon monoxide, and a catalyst comprising at least one of rhodium and cobalt and a hydrolysable organophosphorus ligand. The hydrolysable organophosphorus ligand is a bulky organomonophosphite in some embodiments. In some embodiments, the olefin is $C_3$ or higher. In some embodiments, the olefin is $C_8$ or higher. The amount of organic nitrogen compound in the reaction fluid is 0.25 to 2.5 weight percent based on the total weight of the reaction fluid in some embodiments. In some embodiments, the rate of heavies formation is at least 10 percent less than the rate of heavies formation of when the process is carried out in the absence of the organic nitrogen compound, wherein the hydroformylation process is a continuous process and the rate of heavies formation is measured using gas chromatography over a period of at least seven days. The catalyst comprises rhodium, in some embodiments, and the rate of rhodium loss is at least 25% less than the rate of rhodium loss in the absence of the organic nitrogen compound.

In some embodiments, the present invention relates to a process to reduce heavies formation in a hydroformylation process to produce at least one aldehyde, the process comprising contacting in a reaction zone reactants comprising an olefin, hydrogen and carbon monoxide in the presence of a catalyst comprising an organomonophosphite ligand and at least one of rhodium and cobalt, and 0.1 to 5 weight percent of an organic nitrogen compound based on the total weight of fluid in the reaction zone, the organic nitrogen compound comprising:

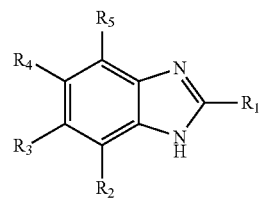

wherein each of $R_1$-$R_5$ are independently hydrogen, an alkyl, or an aryl radical, wherein a plurality of heavies are formed during the hydroformylation process, wherein the rate of heavies formation is at least 10 percent less than the rate of heavies formation of when the process is carried out in the absence of the organic nitrogen compound, and wherein the hydroformylation process is a continuous process and the rate of heavies formation is measured using gas chromatography over a period of at least seven days.

Hydrogen and carbon monoxide are required for the hydroformylation process. These may be obtained from any suitable source, including petroleum cracking and refinery operations. Syngas mixtures are preferred as a source of hydrogen and CO.

Syngas (from synthesis gas) is the name given to a gas mixture that contains varying amounts of CO and $H_2$. Production methods are well known and include, for example: (1) steam reforming and partial oxidation of natural gas or liquid hydrocarbons, and (2) the gasification of coal and/or biomass. Hydrogen and CO typically are the main components of syngas, but syngas may contain carbon dioxide and inert gases such as $CH_4$, $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The olefin starting material reactants that may be employed in a hydroformylation process of this invention include both optically active (prochiral and chiral) and non-optically active (achiral) olefinic unsaturated compounds containing from 2 to 40, preferably 3 to 20, carbon atoms. Such olefinic unsaturated compounds can be substituted or unsubstituted, terminally or internally unsaturated, straight-chain, branched chain or cyclic. Olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403) can be employed. Moreover, such olefin compounds may further contain one or more additional ethylenic unsaturated groups, and mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II. Further such aldehyde products derived therefrom may also contain one or more groups or substituents that do not unduly adversely affect the hydroformylation process or the process of this invention such as described, for example, in U.S. Pat. Nos. 3,527,809, 4,769,498 and the like.

The subject invention is especially useful when implemented in the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene as well as, 1,3-dienes, butadiene, alkyl alkenoates, e.g., methyl pentenoate, alkenyl alkanoates, alkenyl alkyl ethers, alkenols, e.g., pentenols, alkenals (e.g., pentenals), allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Prochiral and chiral olefins useful in the asymmetric hydroformylation that can be employed to produce enantiomeric aldehyde mixtures include those represented by the formula:

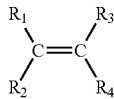

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. The prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360,938 and 5,491,266.

A solvent advantageously is employed in the process, either as a solvent for an aldehyde solution, or a solvent in a hydroformylation process. Any suitable solvent that does not unduly interfere with the hydroformylation process can be used. By way of illustration, suitable solvents for rhodium catalyzed hydroformylation include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, polyethers, alkylated polyethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents employable in the production of aldehydes include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g. nitrobenzene), ethers (e.g. tetrahydrofuran (THF)) and sulfolane. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. In rhodium catalyzed hydroformylation, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,830 and 4,247,486. Indeed, while one may employ, if desired, any suitable solvent at the start-up of a continuous process, the primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of two or more solvents may also be employed.

The catalyst useful in the hydroformylation process comprises a catalytic metal. The catalytic metal can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with preferred metals being rhodium, cobalt, iridium and ruthenium, more preferably rhodium, cobalt and ruthenium, especially rhodium.

The number of available coordination sites on such metals is well known in the art. Thus the catalytic species, which may comprise a complex catalyst mixture, may comprise monomeric, dimeric or higher nuclearity forms, which are preferably characterized by at least one organophosphorous-containing molecule complexed per one molecule of metal, e.g., rhodium.

Illustrative metal-organophosphorous ligand complexes employable in such hydroformylation reactions encompassed by this invention include metal-organophosphorous ligand complex catalysts. The catalysts, as well as methods for their preparation, are well known in the art and include those disclosed in the above-mentioned patents. In general, such catalysts may be preformed or formed in situ as described in such references and consist essentially of metal in complex combination with an organophosphorous ligand. It is believed that carbon monoxide is also present and complexed with the metal in the active species. The active species may also contain hydrogen directly bonded to the metal. Carbon monoxide and/or hydrogen may be present in view of the carbon monoxide and hydrogen gas employed by the hydroformylation reaction.

The permissible organophosphorous ligands that make up the metal-organophosphorous ligand complexes and free organophosphorous ligand include organomonophosphites. Embodiments of the present invention have been found to be particularly useful in reducing heavies formation in hydroformylation processes where the ligand is one or more organomonophosphites. In some embodiments, the ligand is one or more bulky organomonophosphites (or sterically hindered organomonophosphites). Mixtures of such ligands may be employed if desired in the metal-organophosphorous ligand complex catalyst and/or free ligand and such mixtures may be the same or different. It is to be noted that the successful practice of this invention does not depend and is not predicated on the exact structure of the metal-organophosphorous ligand complex species, which may be present in their mononuclear, dinuclear and/or higher nuclearity forms. Indeed, the exact structure is not known. While not intending to be bound to any theory or mechanistic discourse, it appears that the catalytic species may in its simplest form consist essentially of the metal in complex combination with the organophosphorous ligand and carbon monoxide and/or hydrogen.

The term "complex" as used herein means a coordination compound formed by the union of one or more electronically rich molecules or atoms capable of independent existence with one or more electronically poor molecules or atoms, each of which is also capable of independent existence. For example, the organophosphorous ligands employable herein may possess one or more phosphorus donor atoms, each having one available or unshared pair of electrons that are each capable of forming a coordinate bond independently or possibly in concert (e.g., via chelation) with the metal. Carbon monoxide, which is also properly classified as a ligand, can also be present and coordinated to the metal. The ultimate composition of the complex catalyst may also contain an additional ligand, e.g., hydrogen or an anion satisfying the coordination sites or nuclear charge of the metal. Illustrative additional ligands include, for example, alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_3$, $CH_3$, $CH_2=CHCH_2$, $CH_3CH=CHCH_2$, $C_6H_5CN$, $CH_3CN$, $NH_3$, pyridine, $(C_2H_5)_3N$, mono-olefins, diolefins and triolefins, tetrahydrofuran, and the like. The complex species are preferably free of any additional organic ligand or anion that might poison the catalyst or have an undue adverse effect on catalyst performance. It is preferred in the metal-organophosphite ligand complex catalyzed hydroformylation reactions that the active catalysts be free of halogen and sulfur directly bonded to the metal, although such may not be absolutely necessary.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, and triorganophosphite compounds. Such organophosphorous ligands and/or methods for their preparation are well known in the art.

Representative monoorganophosphites may include those having the formula:

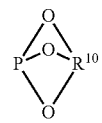

<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306.

Representative diorganophosphites may include those having the formula:

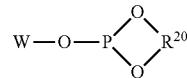

<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 24 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-NR24-arylene wherein $R^{24}$ is as defined above, arylene-S-arylene, and arylene-S-alkylene, and the like. More preferably $R^{20}$ is a divalent aromatic radical such as disclosed more fully, for example, in U.S. Pat. Nos. 4,599,206, 4,717,775, and 4,835,299, PCT Publication No. WO2016/087301, and the like.

Representative of a more preferred class of diorganophosphites are those of the formula:

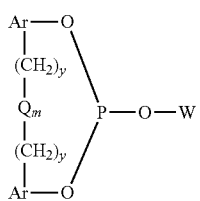

<<III>> wherein W is as defined above, each Ar is the same or different and represents a substituted or unsubstituted aryl radical, each y is the same or different and is a value of 0 or 1, Q represents a divalent bridging group selected from $-C(R^{33})_2-$, $-O-$, $-S-$, $-NR^{24}-$, $Si(R^{35})_2$ and $-CO-$, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835, 299, and PCT Publication No. WO2016/087301.

Representative triorganophosphites may include those having the formula:

<<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 36 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl) cyclohexylphosphite, tris(3,6-di-t-butyl-2-naphthyl)phosphite, bis(3,6,8-tri-t-butyl-2-naphthyl)(4-biphenyl) phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl)(4-sulfonylphenyl) phosphite, and the like. The most preferred triorganophosphite is tris(2,4-di-t-butylphenyl)phosphite. Such triorganophosphites are described in greater detail, for example, in U.S. Pat. Nos. 3,527,809 and 4,717,775, and US Patent Publication No. 2015/0336093.

As noted above, the metal-organophosphorous ligand complex catalysts may be formed by methods known in the art. The metal-organophosphorous ligand complex catalysts may be in homogeneous or heterogeneous form. For instance, preformed rhodium hydrido-carbonyl-organophosphorous ligand catalysts may be prepared and introduced into the reaction mixture of a hydroformylation process. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organophosphorous ligand for the in situ formation of the active catalyst. In a preferred embodiment of this invention, rhodhium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient for the purposes of this invention that carbon monoxide, hydrogen and organophosphorous ligand compound are all ligands that are capable of being complexed with the metal and that an active metal-organophosphorous ligand catalyst is present in the reaction mixture under the conditions used in the hydroformylation reaction. Carbonyl and organophosphorous ligands, if not already complexed with the initial rhodium, may be complexed to the rhodium either prior to or in situ during the hydroformylation process.

By way of illustration, the preferred catalyst precursor composition, in some embodiments, consists essentially of a solubilized rhodium carbonyl organophosphite ligand complex precursor, a solvent and, optionally, free organophosphite ligand. The catalyst precursor composition can be prepared by forming a solution of rhodium dicarbonyl acetylacetonate, an organic solvent and a organophosphite ligand. The organophosphite ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphite ligand complex precursor are soluble can be employed. The amounts of rhodium complex catalyst precursor, organic solvent and organophosphite ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphite ligand, to form the active complex catalyst as explained above. The acetylacetone that is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor and hydroformylation start-up.

Accordingly, the metal-organophosphite ligand complex catalyst used in the hydroformylation process of this invention, in some embodiments, consists essentially of the metal complexed with carbon monoxide and a organophosphite ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphite ligand. Further, such terminology does not exclude the possibility of other organic ligands and/or anions that might also be complexed with the metal. Materials in amounts that unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphite ligand complex catalyst may be present as a result of being ligands bound to a precursor catalyst and/or as a result of in situ formation, e.g., due to the hydrogen and carbon monoxide gases employed in hydroformylation process.

As noted, the hydroformylation process in some embodiments of this invention involves the use of a metal-organophosphorous ligand complex catalyst as described herein. Mixtures of such catalysts can also be employed if desired. The amount of metal-organophosphorous ligand complex catalyst present in the reaction fluid of a given hydroformylation process encompassed by this invention need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal. Analytical techniques for measuring catalytic metal concentrations are well known to the skilled person, and include atomic absorption (AA), inductively coupled plasma (ICP) and X-ray fluorescence (XRF); AA is typically preferred.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above as employable herein. It is preferred that the free organophosphorous ligand be the same as the organophosphorous ligand of the metal-organophosphorous ligand complex catalyst employed. However, such ligands need not be the same in any given process. The hydroformylation process may involve from 0.1 moles or less to 100 moles or higher of free organophosphorous ligand per mole of metal in the reaction medium. In some embodiments, the hydroformylation process is carried out in the presence of from 1 to 50 moles of free organophosphorous ligand per mole of metal present in the reaction medium.

Since it is more preferred to produce non-optically active aldehydes by hydroformylating achiral olefins, the more preferred organophosphorous ligands are achiral type organophosphorous ligands, especially those encompassed by Formula (V) above, and more preferably those of Formulas (VI), (VII) and (VIII) above. If desired, make-up or additional organophosphorous ligand can be supplied to the reaction medium of the hydroformylation process at any time and in any suitable manner, e.g. to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (i.e. alumina, silica, titania, or zirconia) carbon, or ion exchange resins. The catalyst may be supported on, or intercalated inside the pores of, a zeolite, glass or clay; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: *J. Mol. Cat.*, 1991, 70, 363-368; *Catal. Lett.*, 1991, 8, 209-214; *J. Organomet. Chem.*, 1991, 403, 221-227; *Nature*, 1989, 339, 454-455; *J. Catal.*, 1985, 96, 563-573; *J. Mol. Cat.*, 1987, 39, 243-259.

The metal, e.g., rhodium, catalyst may be attached to a thin film or membrane support, such as cellulose acetate or polyphenylenesulfone, as described in, for example, *J. Mol. Cat.*, 1990, 63, 213-221.

The metal, e.g., rhodium, catalyst may be attached to an insoluble polymeric support through an organophosphorus-containing ligand, such as a phosphite, incorporated into the polymer. The supported catalyst is not limited by the choice of polymer or phosphorus-containing species incorporated into it. Descriptions of polymer-supported catalysts may be found in for example: *J. Mol. Cat.*, 1993, 83, 17-35; *Chemtech* 1983, 46; *J. Am. Chem. Soc.*, 1987, 109, 7122-7127.

In the heterogeneous catalysts described above, the catalyst may remain in its heterogeneous form during the entire hydroformylation and catalyst separation process. In another embodiment of the invention, the catalyst may be supported on a polymer that, by the nature of its molecular weight, is soluble in the reaction medium at elevated temperatures, but precipitates upon cooling, thus facilitating catalyst separation from the reaction mixture. Such "soluble" polymer-supported catalysts are described in for example: *Polymer*, 1992, 33, 161; *J. Org. Chem.*, 1989, 54, 2726-2730.

More preferably, the reaction is carried out in the slurry phase due to the high boiling points of the products, and to avoid decomposition of the product aldehydes. The catalyst may then be separated from the product mixture, for example, by filtration or decantation. The reaction fluid may contain a heterogeneous metal-organophosphorous ligand complex catalyst, e.g., slurry, or at least a portion of the reaction fluid may contact a fixed heterogeneous metal-organophosphorous ligand complex catalyst during the hydroformylation process. In an embodiment of this invention, the metal-organophosphite ligand complex catalyst may be slurried in the reaction fluid.

According to embodiments of the present invention, an organic nitrogen compound is added to an aldehyde solution, which can be the reaction fluid in a hydroformylation process. In the context of a hydroformylation process, the organic nitrogen compound can advantageously reduce the rate of heavies formation in the reaction fluid, as discussed in more detail herein. In some embodiments, the organic nitrogen compound can also advantageously reduce the rate of rhodium loss in the reaction fluid.

Suitable organic nitrogen compounds are defined by the formula:

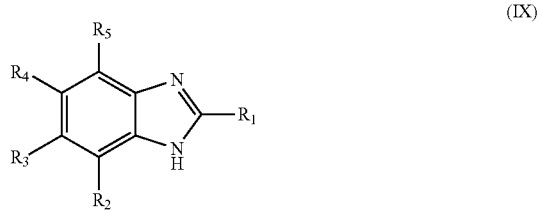

wherein each of $R_1$-$R_5$ is independently hydrogen, an alkyl, or an aryl radical. In one particularly useful embodiment, the organic nitrogen compound is benzimidazole (i.e., each of $R_1$-$R_5$ is hydrogen).

The amount of organic nitrogen compound added to an aldehyde solution such as a reaction fluid from a hydroformylation process is at least 0.10 weight percent based on the total weight of the aldehyde solution. The upper limit on the total amount of organic nitrogen compound that can be added is determined primarily by the solubility limit of the organic nitrogen compound in the aldehyde solution (e.g., hydroformylation reaction fluid). In one embodiment, the concentration range is 0.10 to 5 weight percent based on the total weight of the solution/fluid to which it is added. In another embodiment, the concentration range is 0.10 to 3 weight percent based on the total weight of the solution/fluid to which it is added. In some embodiments, the organic nitrogen compound is added periodically as its concentration may drop over time due to volatility or entrainment during the product/catalyst separation process. The concentration of organic nitrogen compound in the solution can be monitored by conventional means such as gas chromatography or high pressure liquid chromatography of the aldehyde solution (e.g., hydroformylation reaction fluid).

When the aldehyde solution is the reaction fluid in a hydroformylation process, the products of the hydroformylation process may be asymmetric, non-asymmetric or a combination thereof, with the preferred products being non-asymmetric. The process may be conducted in any batch, continuous or semi-continuous fashion and may involve any catalyst liquid and/or gas recycle operation desired.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. Nos. 5,430,194 and 5,681,473, or by the more conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In some embodiments, the hydroformylation reaction fluid employable herein includes any fluid derived from any corresponding hydroformylation process that contains the added organic nitrogen compound and at least some amount of four different main ingredients or components, i.e., the aldehyde product, a metal-organophosphorous ligand complex catalyst, free organophosphorous ligand and an organic solvent for said catalyst and said free ligand, said ingredients corresponding to those employed and/or produced by the hydroformylation process from whence the hydroformylation reaction mixture starting material may be derived. The hydroformylation reaction fluids employable herein can and normally will contain minor amounts of additional ingredients such as those that have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process encompassed by this invention may include any suitable hydroformylation conditions heretofore employed for producing optically active and/or non-optically active aldehydes. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically the carbon monoxide partial pressure of the hydroformylation process of this invention is preferably from 1 to 6,900 kPa, and more preferably from 21 to 5,500 kPa, while the hydrogen partial pressure is preferably from 34 to 3,400 kPa and more preferably from 69 to 2,100 kPa. In general, $H_2$:CO molar ratio of gaseous hydrogen to carbon monoxide in a reaction zone may range from 1:10 to 100:1 or higher, the more preferred hydrogen to carbon monoxide molar ratio being from 1:10 to 10:1.

In general, the hydroformylation process may be conducted at any operable reaction temperature. Advantageously, the hydroformylation process is conducted at a reaction temperature from −25° C. to 200° C. In general, hydroformylation reaction temperatures of 50° C. to 120° C.

are preferred for all types of olefinic starting materials. It is to be understood that when non-optically active aldehyde products are desired, achiral type olefin starting materials and organophosphorous ligands are employed and when optically active aldehyde products are desired prochiral or chiral type olefin starting materials and organophosphorous ligands are employed. The hydroformylation reaction conditions employed will be governed by the type of aldehyde product desired.

The hydroformylation process of this invention may be carried out in one or more reaction zones in one or more suitable reactors such as, for example, a fixed bed reactor, a fluid bed reactor, a tubular reactor, a venturi reactor, a bubble column reactor, a continuous stirred tank reactor (CSTR) or a slurry reactor. The optimum size and shape of the reactor will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The at least one reaction zone employed in this invention may be a single vessel or may comprise two or more discrete vessels. The at least one separation zone employed in this invention may be a single vessel or may comprise two or more discrete vessels. The reaction zone(s) and separation zone(s) employed herein may exist in the same vessel or in different vessels. For example, reactive separation techniques such as reactive distillation, reactive membrane separation and the like may occur in the reaction zone(s).

The hydroformylation process of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be substantially inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the process especially to maintain the desired molar ratio of the starting materials. The reaction steps may be effected by the incremental addition of one of the starting materials to the other. Also, the reaction steps can be combined by the joint addition of the starting materials. The starting materials may be added to each or all the reaction zones in series. When complete conversion is not desired or not obtainable, the starting materials can be separated from the product, for example by distillation, and the starting materials then recycled back into the reaction zone.

The hydroformylation process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation may be carried out in a multistaged reactor such as described, for example, in U.S. Pat. No. 5,728,893. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

As indicated above, it is generally preferred to carry out the hydroformylation process of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorous ligand complex catalyst, and free organophosphorous ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In an embodiment of this invention, the aldehyde product mixtures may be separated from the other components of the crude reaction mixtures in which the aldehyde mixtures are produced by any suitable method. Suitable separation methods include, for example, solvent extraction, crystallization, distillation, vaporization, wiped film evaporation, falling film evaporation, phase separation, filtration and the like or any combination thereof. It may be desired to remove the aldehyde products from the crude reaction mixture as they are formed through the use of trapping agents as described in PCT Publication No. WO 88/08835. One method for separating the aldehyde mixtures from the other components of the crude reaction mixtures is by membrane separation. Such membrane separation can be achieved as set out in U.S. Pat. Nos. 5,430,194 and 5,681,473.

As indicated above, at the conclusion of (or during) the process of this invention, the desired aldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorous ligand and reaction products. When an alpha-mono-olefin reactant is also employed, the aldehyde derivative thereof can also be separated by the above methods.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g. vaporizer/separator, wherein the desired aldehyde product is distilled. In general, distillation pressures ranging from vacuum pressures on up to total gas pressure of 340 kPa should be sufficient for most purposes.

Processes of the present invention advantageously reduce heavies formation in aldehyde solutions. Such aldehyde solutions can be reaction fluids from hydroformylation processes in which aldehyde products are produced. Accordingly, illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricos anal, pentacos anal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl] propionaldehyde, and S-2-(2-methylacetaldehyde)-5-benzoylthiophene.

As discussed elsewherein, the excessive formation of heavies in a hydroformylation process (liquid byproducts that have a normal boiling point that is at least 25° C. above the normal boiling point of the desired product of the hydroformylation process) is generally undesirable, so a process that reduces the rate of heavies formation would be desirable. For purposes of this invention, the rate of heavies formation is determined by measuring the increase in heavies (e.g., dimers and trimers) over time (e.g., at least seven days for a continuous hydroformylation process). In the context of a continuous hydroformylation process, a sample of the process fluid is removed periodically and analyzed by gas chromatography (GC) to determine the weight percent of dimers and trimers, and the results are then plotted as concentration of heavies (y-axis) versus time (x-axis). The slope of the line which best fits the resulting data points quantifies the rate of heavies increase, with the units being weight percent/time (e.g., weight percent/day). For example, liquid samples can be periodically removed from at least one reactor and analyzed by GC to determine the weight percent of heavies in the reaction fluid; in a preferred embodiment, a liquid sample is removed at the desired interval(s) from each reactor, and the results averaged to give heavies concentrations representative of the entire process. In another embodiment, a batchwise process may be sampled at the beginning and at intervals throughout the duration of the run to determine heavies formation rate, with the GC analyses and calculation performed as described above. The above analysis assumes that other process parameters (e.g., reaction fluid volume, vaporizer feed-to-tails ratio, unit temperatures, vaporizer pressure, and the like) within the hydroformylation reaction system remain essentially constant.

Methods of determining the weight percent of heavy byproducts include, but are not limited to GC area percent analysis, GC external standard analysis (ESTD) and GC internal standard analysis (ISTD). The response of a GC detector to a particular analyte is determined by the chemical composition and concentration of the analyte in the sample. Analytes of similar chemical composition will demonstrate similar response on a given detector, thus a response factor determined by injecting a measured amount of a known compound as part of a calibration standard, may also be applied to other chemically similar components. For example, the response factor determined for one C8 olefin may be applied to other C8 olefin isomers; likewise for dimer isomers, trimer isomers, etc. Determining the concentration of the individual heavy compounds is not critical; thus for the sake of quantifying and calculating heavies formation rate it is acceptable to combine dimer peaks together and trimer peaks together. The concept of grouping GC peaks to report the collective concentration of similar compounds is well known to the skilled person (see, e.g., "Guide to ASTM Methods for the Analysis of Petroleum Products and Lubricants, ASTM International, 2007, p. 134). In general, compounds of similar structures will have comparable volatility and polarity, and will thus elute at similar retention times on the gas chromatogram. For example, a plurality of dimer peaks will have similar retention times and may be grouped together, and their collective concentration reported as "weight percent dimers"; likewise for "weight percent trimers", etc.

The general principles of GC method development are well known to the skilled person (see for example "Optimization of Chromatographic Selectivity: A Guide to Method Development; Volume 35 of Journal of Chromatography" Library, Elsevier, 1986). While the exact method of the GC analysis is not critical, the conditions employed should be sufficient to discriminate between olefins, aldehyde products, dimers, trimers, and additional heavy byproducts. The general identity of by-products can be determined by conventional means such as GC-Mass Spectrometry as well as independent synthesis such as described in U.S. Pat. No. 4,148,830. In one embodiment, at least one fused silica capillary column with a non-polar bonded stationary phase is utilized in a chromatograph with temperature programming capability and a flame ionization detector. In general, the resolution of the plurality of peaks will improve with the length of the column employed. In one embodiment, a 30 meter column is employed; in a preferred embodiment a 50 meter column is employed, and in a most preferred embodiment a 100 meter column is employed. If desired, two or more columns may be connected in series to increase resolution; the columns thus employed may have the same or different stationary phases and dimensions.

For purposes of this invention, the term "heavies formation rate" means the rate at which aldehyde dimers and trimers form in the hydroformylation process. Heavies formation rate is expressed as "weight percent/day" and is calculated as follows:

$$\frac{\text{(weight percentage of dimers + trimers)}_{final} - \text{(weight percentage of dimers + trimers)}_{initial}}{\text{number of days in the test period}}$$

The (weight percentage of dimers+trimers)$_{final}$ and (weight percentage of dimers+trimers)$_{initial}$ can be measured as described above. For example, if the heavies formation rate in the absence of the process of the invention is 3 wt. %/day, and the process of the invention reduces the rate of heavies formation to 1.5 wt. %/day, a 50% reduction in the rate of heavies formation would be realized. By utilizing the organic nitrogen compound as specified herein, processes of the present invention can advantageously reduce the rate of heavies formation in the reaction fluid.

An additional advantage for some embodiments of the present invention is a reduction in the rate of rhodium loss that often occurs in a hydroformylation process. As used herein, the term "rate of rhodium loss" means the change in rhodium concentration over time. The concentration of rhodium can be measured using conventional means such as atomic absorption (AA). The change in concentration is expressed as part per million (ppm) rhodium lost per day (ppm/day), and is calculated as follows:

$$\frac{(ppm \text{ rhodium})_{initial} - (ppm \text{ rhodium})_{final}}{\text{number of days in the test period}}$$

In another embodiment the rate of rhodium loss may be determined based on multiple data points by plotting the concentration of rhodium in ppm (y-axis) over a number days (x-axis); the slope of the line thus described will determine the rate of rhodium loss in ppm/day. For purposes of the invention, decreasing the rate of rhodium loss from 10 ppm/day down to 5 ppm/day constitutes a 50% reduction in the rate of rhodium loss.

Some embodiments of the invention will now be described in more detail in the following Examples.

EXAMPLES

All parts and percentages in the following examples are by weight unless otherwise indicated. Pressures are given as absolute pressure unless otherwise indicated. The mixed C9 aldehyde was obtained from the hydroformylation of mixed octenes, and was distilled prior to use unless otherwise noted. The mixed C9 aldehyde used in the examples contains 96.8 wt. % mixed C9 aldehydes, 2.2 wt. % dimers, and 0.7 wt % trimers unless otherwise noted. The butyraldehyde used in the examples is obtained from the hydroformylation of propylene and distilled prior to use; the total heavies concentration is ~1 wt. %.

Sample analyses for C9 aldehyde experiments are performed by gas chromatography (GC) using the following parameters:
Column—Petrocol DH 100 m×0.25 mm; 0.5 µfilm
Injection—1 µL; split ratio 150:1
Detector—FID at 270° C.
Oven program—40° C. for 40 minutes, to 220° C. at 10° C./min; hold 5 min, to 260° C. at 5° C./min; hold 19 minutes, to 270° C.; hold 48 minutes.

Component quantitation is based on external standard calibration using representative compounds; the multiple dimer peaks and trimer peaks are grouped for reporting purposes.

Sample analyses for C4 aldehyde experiments are performed by GC using the following parameters:
Column—DB-1 30 m×0.32 mm; 0.5 µfilm
Injection—1 µL; split ratio 100:1
Detector—FID at 300° C.
Oven program—35° C. for 10 min, to 150° C. at 8° C./min, to 270° C. at 15° C./min; hold for 30 minutes.

Components quantitation is based on external standard calibration; heavies are grouped as dimers and trimers.

Unless otherwise noted, heavies formation rate is expressed as "weight percent/day" and is calculated as follows:

$$\frac{\text{(weight percentage of dimers + trimers)}_{final} - \text{(weight percentage of dimers + trimers)}_{initial}}{\text{number of days in the test period}}$$

Rhodium concentration is determined by atomic absorption (AA) using an air/acetylene flame. It has been found that this technique will not reliably quantify clustered rhodium; thus this method may be used to indicate "rhodium loss" (e.g., undetectable rhodium is clustered or otherwise no longer in solution and thus not active for hydroformylation). Rate of rhodium loss is calculated as:

(ppm rhodium)$_{initial}$−(ppm rhodium)$_{final}$/number of days in the test period Color change (starting from a colorless or light yellow solution), such as darkening or formation of black film or solids is also indicative of rhodium catalyst degradation.

Ligand A used in the examples is tris(2,4-di-tert-butylphenyl) phosphite:

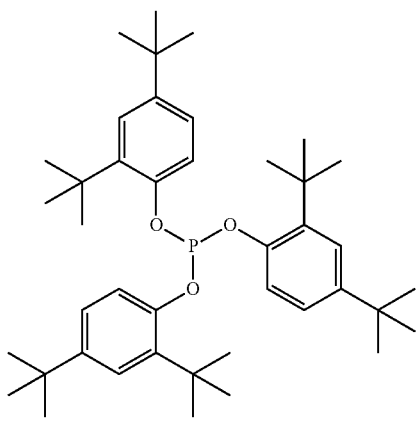

Ligand A

Comparative Experiment A

A Fischer-Porter tube is charged with mixed C9 aldehyde (about 10 mL) under an atmosphere of nitrogen. The aldehyde is stirred in an oil bath at 115° C. overnight, after which a sample is removed for GC analysis.

Inventive Example 1

The procedure of Comparative Experiment A is followed with the exception of the addition of benzimidazole (Bzim; 2.5 wt. %) to the aldehyde.

The results for Comparative Experiment A and Example 1 are shown in Table 1.

TABLE 1

|        | Bzim added (wt. %) | C9 Ald. (wt %) | Dimers (wt %) | Trimers (wt %) | Dimers + Trimers (wt %) | heavies formation rate (wt. %/day) |
|--------|--------------------|----------------|---------------|----------------|-------------------------|------------------------------------|
| C.E. A | 0                  | 76.2           | 9.8           | 11.9           | 21.7                    | 18.8                               |
| I.E. 1 | 2.5                | 83.8           | 7.1           | 6.1            | 13.2                    | 10.3                               |

The formation of both dimers and trimers is slowed by the presence of benzimidazole; a benefit of 45% reduction in the rate of heavies formation is demonstrated.

Comparative Experiment B

A Fischer-Porter tube is charged with mixed C9 aldehyde (20 mL), rhodium dicarbonyl acetylacetonate (approximately 300 ppm rhodium) and Ligand A (about 10 equivalents per rhodium). The solution is sparged with 1:1 CO:H2 for about one hour, after which it is purged briefly with nitrogen and sealed under 10 psi total pressure in a 115° C. oil bath. The solution is sampled periodically for GC analysis.

Inventive Example 2

The procedure of Comparative Experiment B is followed, with the exception of the addition of benzimidazole (2.0 wt. %).

Inventive Example 3

The procedure of Comparative Experiment B is followed, with the exception of the addition of benzimidazole (1.0 wt. %).

The results for heavies formation occurring over a 5 day period in Comparative Experiment B and Inventive Examples 2 and 3 are shown in Table 2.

TABLE 2

|        | Bzim added (wt %) | C9 Ald. (wt %) | Dimers (wt %) | Trimers (wt %) | Dimers + Trimers (wt %) | heavies formation rate (wt %/day) |
|--------|-------------------|----------------|---------------|----------------|-------------------------|-----------------------------------|
| C.E. B | 0                 | 64.2           | 14.4          | 12.4           | 26.8                    | 4.8                               |
| I.E. 2 | 2.0               | 80.6           | 5.0           | 9.4            | 14.4                    | 2.3                               |
| I.E. 3 | 1.0               | 80.5           | 6.4           | 8.9            | 15.2                    | 2.5                               |

The concentration of rhodium over time for Comparative Experiment B and Inventive Examples 2 and 3 is summarized in Table 3.

TABLE 3

|        | Rhodium (ppm) by AA | | | | |
|--------|---------|-------------|--------------|--------------|----------------------------------|
|        | Charge  | After 1 day | After 4 days | After 5 days | Rate of rhodium loss (ppm/day)   |
| C.E. B | 327     | 283         | 225          | 208          | 15.0                             |
| I.E. 2 | 259     | 260         | 268          | 259          | 0                                |
| I.E. 3 | 284     | 289         | 287          | 277          | 1.4                              |

The rate of rhodium loss is decreased by ≥90%. The solution in Comparative Experiment B was very dark brown, while the solutions in Inventive Examples 2 and 3 remained clear yellow, further indicating that benzimidazole enhances rhodium stability in a rhodium-bulky organomonophosphite catalyst solution.

Comparative Experiment C

The procedure of Comparative Experiment B is followed, with the exception of samples being pulled at different intervals.

Inventive Example 4

The procedure of Comparative Experiment C is followed, with the exception of the amount of benzimidazole added (0.5 wt %).

Inventive Example 5

The procedure of Comparative Experiment C is followed, with the exception of the amount of benzimidazole added (0.25 wt %).

The results for Comparative Experiment C and Inventive Examples 4 and 5 after 6 days at 115° C. are summarized in Table 4.

TABLE 4

|  | Bzim added (wt %) | C9 Ald. (wt %) | Dimers (wt %) | Trimers (wt %) | Dimers + Trimers (wt %) | heavies formation rate (wt %/day) |
|---|---|---|---|---|---|---|
| C.E. C | 0 | 58.4 | 12.0 | 11.3 | 23.2 | 3.5 |
| I.E. 4 | 0.5 | 73.2 | 3.9 | 9.6 | 13.5 | 1.8 |
| I.E. 5 | 0.25 | 72.5 | 3.5 | 10.2 | 13.6 | 1.8 |

The rate of heavies formation is reduced by nearly 50% in Inventive Examples 4 and 5. Collectively, the results of Tables 2 and 4 show that the invention is effective across a broad organic nitrogen compound concentration range.

Comparative Experiment D

The procedure of Comparative Experiment B is followed, with the exception of samples being pulled at different intervals.

Comparative Experiment E

The procedure of Comparative Experiment C is followed, with the exception of the amount of benzimidazole added (0.07 wt %).

Comparative Experiment F

The procedure of Comparative Experiment C is followed, with the exception of the amount of benzimidazole added (0.03 wt %).

The results for Comparative Experiments D-F after 4 days at 115° C. are summarized in Table 5.

TABLE 5

|  | Bzim added (wt %) | Aldehyde (wt %) | Dimers (wt %) | Trimers (wt %) | Dimers + Trimers (wt %) | heavies formation rate (wt %/day) |
|---|---|---|---|---|---|---|
| C.E. D | 0 | 87.6 | 1.9 | 9.8 | 11.7 | 2.2 |
| C.E. E | 0.07 | 86.8 | 2.6 | 9.2 | 11.8 | 2.2 |
| C.E. F | 0.03 | 86.0 | 2.6 | 10.5 | 13.1 | 2.6 |

Table 5 shows that benzimidazole concentrations below 0.10 wt % do not give the result of the invention.

Comparative Experiment G

A catalyst comprised of rhodium (400 ppm), ligand A (0.5 wt %), mixed C9 aldehydes and 50 wt. % C9 aldehyde-derived heavies (20 mL) is charged to a Fischer-Porter tube. The tube is sparged with 1:1 CO:H2 for about one hour and then sealed under 10 psi total pressure at 115° C. The solution is sampled periodically for GC analysis.

Inventive Example 6

The procedure of Comparative Experiment D is followed, with the exception of the addition of benzimidazole (0.50 wt %).

Inventive Example 7

The procedure of Comparative Experiment D is followed, with the exception of the addition of benzimidazole (1.00 wt %).

The results of Comparative Experiment G and Inventive Examples 6 and 7 after 9 days are shown in Table 6.

TABLE 6

|  | Bzim added (wt %) | C9 Ald. (wt %) | Dimers (wt %) | Trimers (wt %) | Dimers + Trimers (wt %) | heavies formation rate (wt %/day) |
|---|---|---|---|---|---|---|
| C.E. G | 0 | 28.2 | 15.5 | 47.9 | 63.4 | 1.5 |
| I.E. 6 | 0.5 | 36.5 | 5.2 | 52.7 | 57.9 | 0.9 |
| I.E. 7 | 1 | 38.7 | 5.7 | 49.8 | 55.5 | 0.6 |

The formation of heavies is slowed, particularly in respect to the lower dimer concentrations in the solutions of the invention.

Comparative Experiment H

A Fischer-Porter tube is charged with butyraldehyde (10 mL) and sealed under 10 psi nitrogen pressure. The aldehyde is stirred in a 115° C. oil bath and sampled periodically for GC analysis.

Inventive Example 8

The procedure of Comparative Experiment E is followed, with the exception of the addition of benzimidazole (1.8 wt. %).

Results for Comparative Experiment H and Inventive Example 8 after 2 days appear in Table 7.

TABLE 7

|  | Bzim added (wt %) | Trimers (wt %) | heavies formation rate (wt %/day) |
|---|---|---|---|
| C.E. H | 0 | 23.5 | 11.3 |
| I.E. 8 | 1.8 | 12.2 | 5.6 |

The results of Table 7 show that the process of the invention is independent of the nature of the aldehyde.

Comparative Experiments I-S

The procedure of Comparative Example A is followed, with the exception of the use of different organic nitrogen compounds and sampling intervals. These organic nitrogen compounds are outside the scope of the present invention. The results are summarized in Tables 8 and 9.

TABLE 8

| | Organic nitrogen compound | compound (wt. %) | C9 Ald. (wt %) | Dimers (wt %) | Trimers (wt %) | Dimers + Trimers (wt %) | heavies formation rate (wt %/day) |
|---|---|---|---|---|---|---|---|
| C.E. I | Bis(2,2,6,6-tetramethyl-4-piperidyl) sebacate | 0.9 | 78.6 | 6.8 | 13.4 | 20.2 | 2.9 |
| C.E. J | 7-ethylindole | 1.6 | 78.9 | 4.5 | 13.4 | 17.9 | 2.5 |
| C.E. K | 5-chlorobenzotriazole | 0.6 | 81.3 | 3.8 | 13.9 | 17.7 | 2.5 |
| C.E. L | 2,5-dimethylpyrrole | 1.1 | 82.2 | 2.4 | 13.7 | 16.1 | 2.2 |
| C.E. M | 2-acetylpyrrole | 1.1 | 83.5 | 1.8 | 14 | 15.8 | 2.2 |
| C.E. N | control | 0.0 | 83.1 | 2 | 14.1 | 16.2 | 2.2 |

TABLE 9

| | Organic nitrogen compound | compound (wt %) | C9 Ald. (wt %) | Dimers (wt %) | Trimers (wt %) | Dimers + Trimers (wt %) | heavies formation rate (wt %/day) |
|---|---|---|---|---|---|---|---|
| C.E. O | benzotriazole | 1.85 | 86.1 | 2.8 | 9.8 | 12.6 | 3.2 |
| C.E. P | 5-methoxybenzimidazole | 0.75 | 83.7 | 3.8 | 9.2 | 13.0 | 3.4 |
| C.E. Q | indazole | 0.89 | 85.4 | 3.1 | 9.7 | 12.8 | 3.3 |
| I.E. 9 | 5,6-dimethylbenzimidazole | 1.99 | 81.0 | 4.0 | 7.7 | 11.6 | 2.9 |
| C.E. R | control | 0 | 82.0 | 2.8 | 10.0 | 12.8 | 3.3 |

None of the organic nitrogen compounds tested in Comparative Experiments I-N and O-R provide the result of the current invention. The organic nitrogen compound in Inventive Experiment 9 provides a reduction in the rate of heavies formation of 12%.

What is claimed is:

1. A process to reduce heavies formation in a solution comprising one or more aldehydes, the process comprising: providing 0.1 to 5 wt. percent of an organic nitrogen compound based on the total weight of the aldehyde solution, the organic nitrogen compound comprising:

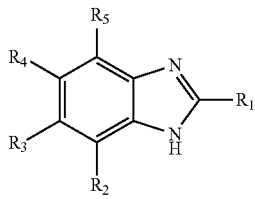

wherein each of $R_1$-$R_5$ are independently hydrogen, an alkyl, or an aryl radical.

2. The process of claim 1 wherein the organic nitrogen compound comprises benzimidazole.

3. The process of claim 1, wherein the aldehyde solution is a reaction fluid in a hydroformylation process comprising an olefin, hydrogen, carbon monoxide, and a catalyst comprising at least one of rhodium and cobalt and a hydrolysable organophosphorus ligand.

4. The process of claim 3, wherein the hydrolysable organophosphorus ligand is a bulky organomonophosphite.

5. The process of claim 4 wherein the catalyst comprises rhodium and the rate of rhodium loss is at least 25% less than the rate of rhodium loss in the absence of the organic nitrogen compound.

6. The process of claim 3, wherein a plurality of heavies are formed during the hydroformylation process, wherein the rate of heavies formation is at least 10 percent less than the rate of heavies formation of when the process is carried out in the absence of the organic nitrogen compound, and wherein the hydroformylation process is a continuous process and the rate of heavies formation is measured using gas chromatography over a period of at least seven days.

7. The process of claim 3, wherein the amount of benzimidazole in the reaction fluid is 0.25 to 2.5 weight percent based on the total weight of the reaction fluid.

8. The process of claim 3, wherein the olefin is $C_3$ or higher.

9. The process of claim 3, wherein the olefin is $C_8$ or higher.

10. The process of claim 1, wherein the aldehyde is $C_3$ or higher.

11. A process to reduce heavies formation in a reaction fluid in a hydroformylation process comprising an olefin, hydrogen, carbon monoxide, and a catalyst comprising at least one of rhodium and cobalt and a hydrolysable organophosphorus ligand, the reaction fluid comprising one or more aldehydes, the process comprising: providing 0.1 to 5 wt. percent of an organic nitrogen compound based on the weight of the reaction fluid, the organic nitrogen compound comprising:

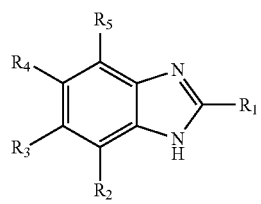

wherein each of $R_1$-$R_5$ are independently hydrogen, an alkyl, or an aryl radical, wherein a plurality of heavies are formed during the hydroformylation process, wherein the rate of heavies formation is at least 10 percent less than the rate of heavies formation of when the process is carried out in the absence of the organic nitrogen compound, and wherein the hydroformylation process is a continuous process and the rate of heavies formation is measured using gas chromatography over a period of at least seven days.

* * * * *